United States Patent [19]

Yamada et al.

[11] Patent Number: 4,843,066
[45] Date of Patent: Jun. 27, 1989

[54] NOVEL ADENOSINE DERIVATIVES AND PHARMACEUTICAL COMPOSITION CONTAINING THEM AS AN ACTIVE INGREDIENT

[75] Inventors: Toshio Yamada, Hyogo; Ken-ichi Kageyama, Kyogo, both of Japan

[73] Assignee: Nippon Zoki Pharmaceutical Co., Ltd., Osaka, Japan

[21] Appl. No.: 123,519

[22] Filed: Nov. 20, 1987

[30] Foreign Application Priority Data

Nov. 27, 1986 [JP] Japan .................. 61-283904

[51] Int. Cl.$^4$ .................. A61K 31/70; C07H 19/16
[52] U.S. Cl. .................. 514/45; 514/46; 536/24; 536/26
[58] Field of Search .................. 536/24, 26; 514/45, 514/46

[56] References Cited

U.S. PATENT DOCUMENTS

| | | | |
|---|---|---|---|
| 3,248,380 | 8/1966 | Moffatt et al. | 536/26 |
| 3,590,029 | 6/1971 | Koch et al. | 536/26 |
| 3,819,612 | 6/1974 | Imai et al. | 536/26 |

FOREIGN PATENT DOCUMENTS

| | | | |
|---|---|---|---|
| 0152944 | 8/1985 | European Pat. Off. | 514/46 |

OTHER PUBLICATIONS

Kochetkov et al., Organic Chemistry of Nucleic Acids, Part B, Plenum Press, N.Y., N.Y., 1972, pp. 459–460.

*Primary Examiner*—Ronald W. Griffin
*Assistant Examiner*—L. Eric Crane
*Attorney, Agent, or Firm*—Armstrong, Nikaido, Marmelstein, Kubovcik & Murray

[57] ABSTRACT

Novel adenosine compounds of the formula (I):

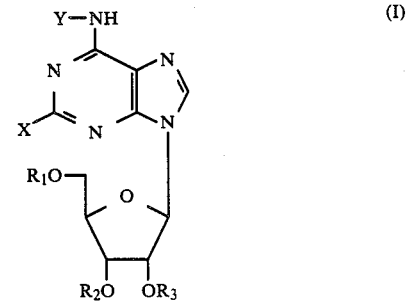

wherein $R_1$, $R_2$ and $R_3$ are hydrogen or a lower alkyl group; X is hydrogen, a lower alkyl group, an amino group or halogen; and Y is hydrogen or a lower alkyl group, exhibit utility as antihypertensive agents.

11 Claims, No Drawings

NOVEL ADENOSINE DERIVATIVES AND PHARMACEUTICAL COMPOSITION CONTAINING THEM AS AN ACTIVE INGREDIENT

BACKGROUND OF THE INVENTION

The present invention relates to novel adenosine derivatives, pharmaceutically acceptable salts thereof and pharmaceutical compositions containing them as an active ingredient.

Hypertension is one of the most serious risk factors causing cerebral apoplexy and cardiopathy which are included in the major causes of death. The frequency of hypertension is increasing as the population becomes older, and it is estimated that about 20% persons of the total population in Japan are suffering from hypertension. Thus various antihypertensive agents such as diuretics, sympathetic depressant drugs, direct-acting vasodilators, calcium antagonists or angiotensin antagonists have been developed and used for a treatment of hypertension. However, for example, side effects such as bradycardia causing various symptoms such as tiredness, depression of activity, disturbance of cerebral circulation or cerebral ischemia are sometimes observed under the treatment with sympathetic depressant drugs. Therefore, the developments of antihypertensive agents having greater safety and effectiveness are desired. As a result of investigations for orally administrable antihypertensive compounds, the inventors have found adenosine derivatives having vasodilatively hypotensive effect as well as low toxicity and good safety.

An object of the present invention is to provide new adenosine derivative and pharmaceutically acceptable salts thereof having an excellent antihypertensive effect. Another object of the present invention is to provide pharmaceutical compositions containing these adenosine derivatives or pharmaceutically acceptable salts thereof as an active ingredient.

DETAILED DESCRIPTION OF THE INVENTION

The adenosine derivatives of the present invention are represented by the following general formula (I):

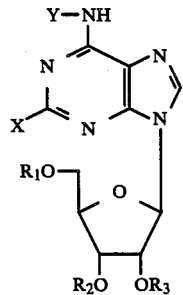

wherein each of $R_1$, $R_2$ and $R_3$, which may be the same or different, is hydrogen or a lower alkyl group; X is hydrogen, a lower alkyl group, an amino group or halogen; and Y is hydrogen or a lower alkyl group.

Each of $R_1$, $R_2$ and $R_3$, which may be the same or different, represents hydrogen or a lower alkyl group, preferably a straight or branched alkyl group having 1 to 5 carbon atoms, such as methyl, ethyl, propyl, isopropyl, butyl, isobutyl, sec-butyl, tert-butyl, pentyl, isopentyl, neopentyl or tert-pentyl.

X represents hydrogen; a lower alkyl group, preferably a straight or branched alkyl group having 1 to 5 carbon atoms, such as methyl, ethyl, propyl, isopropyl, butyl, isobutyl, sec-butyl, tert-butyl, pentyl, isopentyl, neopentyl or tert-pentyl; an amino group; or halogen such as fluoride, chloride, bromide or iodide.

Y represents hydrogen or a lower alkyl group, preferably a straight or branched alkyl group having 1 to 5 carbon atoms, such as methyl, ethyl, propyl, isopropyl, butyl, isobutyl, sec-butyl, tert-butyl, pentyl, isopentyl, neopentyl or tert-pentyl.

The adenosine derivatives of the present invention include pharmaceutically acceptable salts of the compounds having formula (I) above, for example, salts with alkali metal such as sodium or potassium, with alkaline-earth metal such as calcium or barium, or with other metals such as aluminum, or salts with an organic base such as ammonia or the like. These salts can be prepared from free adenosine derivatives or other salts of these derivatives by a known method.

When optical isomers exist in the compounds of the invention, the present invention includes any of the dl, d and l-isomers.

The adenosine derivatives of the present invention can be prepared as follows.

(1) Adenosine or adenosine derivatives having a lower alkyl group, an amino group or halogen at the 2-position were alkylated at the 2'-O- or 3'-O-position by an alkylating agent to give the compounds of the present invention. A diazoparaffin, such as diazomethane, diazoethane, diazopropane or diazobutane, can be used as the alkylating agent. The appropriate solvent which does not inhibit the reaction such as 1,2-dimethoxyethane can be preferably used. This O-alkylating reaction can be carried out as follows: (i) The reaction mixture is reacted for several minutes to several hours at room temperature in the presence of a catalyst such as p-toluenesulfonic acid. (ii) The starting material is dissolved in about 80° C. hot water and the alkylating agent such as diazoparaffin is added thereto, and the reaction mixture is reacted for several hours to a day.

(2) Both 3'-O- and 5'-O-positions of the adenosine derivatives are protected by tetraisopropyldisiloxane (TIPDS) group to carry out O-alkylation selectively at the 2'-Oposition. A 6-chloropurine-9-riboside and TIPDS·Cl$_2$ (1,3-dichloro-1,1,3,3-tetraisopropyldisiloxane dichloride) are stirred for several hours at room temperature to protect the 3'-O- and 5'-O-positions, and then the 2'-O-position of the compound protected by TIPDS can be selectively alkylated by an alkylating agent such as methyl iodide, ethyl iodide, propyl iodide or butyl iodide in the presence of catalyst such as silver oxide. After the 2'-O-alkylation, an amination or alkylamination at the 6-position can be carried out by reacting with ammonia or alkylamine such as methylamine, ethylamine, propylamine or butylamine with heating. The protecting group, TIPDS, can be removed by a conventional method to give the compounds of the present invention.

(3) In the similar manner, both 2'-O- and 3'-O-positions of the adenosine derivatives are protected by isopropylidene group to carry out O-alkylation selectively at the 5'-O-position. Namely, A 6-chloropurine-9-riboside and 2,2-dimethoxypropane are reacted for several hours at room temperature in the presence of catalyst such as p-toluenesulfonic acid to carry out isopropylidenation. After the 5'-O-alkylation, an amination or alkylamination at 6-position can be carried out as mentioned above. The protecting group, isopropylidene group, can be removed by a conventional method, for example, treatment with formic acid, to give the compounds of the present invention.

The resulting compounds of the present invention can be purified by known methods such as distillation chromatography and recrystallization. Identification is established through, inter alia, melting point, elemental analysis, IR, NMR, UV, mass spectrum, etc.

EXAMPLE

The following examples, which are illustrative only and not intended to limit the scope of the invention, describe the preparation of the compounds of the present invention.

Example 1

[METHOD 1]

10 g of adenosine was suspended in 2 l of 1 mmole methanol solution of tin chloride dihydrate. 500 ml of 0.4–0.5M 1,2-dimethoxyethane solution of diazomethane was added to the solution with stirring. After stirring for 2 hours at room temperature, the solution was evaporated to dryness under reduced pressure. The residue was purified by ion exchange column chromatography and recrystallized from ethanol to give 2'-O-methyladenosine (Compound 1) and 3'-O-methyladenosine (Compound 2).

—Compound 1— yield: 33.5% m.p.: 205.5°–206° C.

NMR($D_2O$): $\delta$=3.43(3H,s), 3.93(1H,dd,J=2.4, 12.7 Hz), 3.86(1H,dd,J=2.9, 12.7 Hz), 4.26(1H,m), 4.40(1H,dd,J=5.9, 5.9 Hz), 4.56(1H,dd,J=4.9, 5.9 Hz), 6.01(1H,d,J=5.9 Hz), 8.01(1H,s), 8.20(1H,s)

—Compound 2— yield: 43.4% m.p.: 177.5°–178° C.

NMR($D_2O$): $\delta$=3.54(3H,s), 3.83(1H,dd,J=2.9, 13.2 Hz), 3.94(1H,dd,J=3.4, 13.2 Hz), 4.11(1H,dd,J=4.4, 4.4 Hz), 4.37(1H,m), 4.87(1H,dd,J=5.9, 5.9 Hz), 6.00(1H,d,J=5.9 Hz), 8.11(1H,s), 8.25(1H,s)

[METHOD 2]

5 g of adenosine was dissolved in 160 ml of 80° C. hot water, and 500 ml of 1,2-dimethoxyethane solution of diazomethane was added thereto with stirring. The solution was cooled to room temperature with stirring and was evaporated to dryness under reduced pressure. The starting material, adenosine, was removed by ODS column chromatography to give a mixture of Compound 1 and Compound 2. 2.6 g of the mixture was separated by ion exchange column chromatography to obtain Compound 1 and Compound 2.

Example 2

(i) 10 g of inosine was treated in the same manner as Example 13 (i) and (ii) mentioned later to give 12 g of 6-chloro-9-(2,3,5-O-triacetyl-β-D-ribofuranosyl-9H-purine (yield: 78%).

(ii) 200 ml of 20% ammonia methanol solution was added to the resulting product, and the solution was stirred for 4 hours at room temperature. The solution was concentrated under reduced pressure and ethyl acetate was added thereto to precipitate 5.6 g of 6-chloro-9-β-D-ribofuranosyl-9H-purine (yield: 69%).

(iii) 4 g of 6-chloro-9-β-D-ribofuranosyl-9H-purine was suspended in 70 ml of pyridine. After 4.5 g of TIPDS·$Cl_2$ was added thereto and the solution was stirred for 2 hours at room temperature, the reaction mixture was purified by silica gel column chromatography to give 6.8 g of 6-chloro-9-(3,5-O-TIPDS-β-D-ribofuranosyl)-9H-purine (yield: 92%).

(iv) 2 g of the resulting product was dissolved in 70 ml of benzene, and 70 ml of ethyl iodide and 3 g of silver oxide were added to the solution. The solution was refluxed with heating. The reactant was checked every thirty minutes and ethyl iodide and silver oxide were added thereto. After filtering off silver iodide, the filtrate was concentrated to dryness, and the residue was dissolved in 20% ammonia methanol solution. The solution was heated for 6 hours at 80° C. in an autoclave and purified by silica gel column chromatography to give 1.8 g of 2'-O-ethyl-3'5'-O-TIPDS-adenosine.

(v) 1.5 g of the resulting product, 1 g of potassium fluoride and 3.7 g of tetraethylammonium chloride were dissolved in 65 ml of acetonitrile, and the solution was stirred for 15 hours at room temperature. After desalting, the solution was purified by ion exchange column chromatography to give 575 mg of 2'-O-ethyladenosine (Compound 3).

yield: 68%

NMR($D_2O$): $\delta$=1.09(3H,dd,J=6.8, 6.8 Hz), 3.52–3.72(2H,m), 3.84(1H,dd,J=3.4, 12.7 Hz), 3.91(1H,dd,J=2.9, 12.7 Hz), 4.31(1H,m), 4.56(1H,dd,J=3.4, 5.4 Hz), 4.64(1H,dd,J=5.4, 6.4 Hz), 6.11(1H,d,J=6.4 Hz), 8.25(1H,s), 8.34(1H,s)

Using butyl iodide instead of ethyl iodide, 2'-O-n-butylation was carried out in the same manner to give 2'-O-butyladenosine (Compound 4).

NMR($D_2O$): $\delta$=0.64(3H,t,J=7.3 Hz), 1.05(2H,m), 1.34(2H,m), 3.47(1H,m), 3.64(1H,m), 3.84(1H,dd,J=3.4, 12.7 Hz), 3.92(1H,dd,J=2.9, 12.5 Hz), 4.32(1H,m), 4.53(1H,dd,J=2.4, 5.4 Hz), 4.62(1H,dd,J=5.4, 6.8 Hz), 6.08(1H,d,J=6.84 Hz), 8.24(1H,s), 8.34(1H,s)

Example 3

[METHOD 1]

(i) 6 g of 5-amino-1-β-D-ribofuranosyl-4-imidazolecarboxamide was dissolved in 250 ml of 1N sodium ethoxide. 20 ml of ethyl acetate was added thereto, and the reaction mixture was heated for 3 hours at 120° C. After the solution was neutralized and desalted, 70 ml of acetic anhydride and 70 ml of pyridine were added thereto and the solution was stirred for 12 hours at room temperature. The solvent was distilled off under reduced pressure to give 9 g of 2-methyl-2',3',5'-O-triacetylinosine (yield: 95%).

(ii) 10.3 g of the resulting product was dissolved in 140 ml of chloroform. 14 ml of thionyl chloride and 3.5 ml of dimethylformamide were added thereto, and the solution was refluxed with heating for 2 hours. The reaction mixture was poured into ice cold water, and the separated chloroform layer was washed to be neutralized. After drying over sodium sulfate anhydride, the solvent was distilled off to give 9.5 g of 6-chloro-2-methyl-9-(2,3,5-O-triacetyl-β-D-ribofuranosyl)-9H-purine (yield: 88.7%).

(iii) The resulting product was dissolved in 150 ml of 20% ammonia methanol solution and heated for 8 hours in an autoclave. The solution was concentrated to dryness under reduced pressure and desalted to give 5.5 g of 2-methyladenosine (yield: 87.9%).

(iv) 2-methyladenosine was methylated in the same manner as Example [METHOD 1] to give 1.8 g of 2,2'-O-dimethyladenosine (Compound 5) and 2.9 g of 2,3'-O-dimethyladenosine (Compound 6).

—Compound 5— yield: 34.3%
m.p.: 169°–170° C.
NMR($D_2O$): $\delta=2.47(3H,s)$, 3.39(3H,s), 3.83(1H,dd,J=2.44, 12.7 Hz), 3.91(1H,dd,J=2.44, 12.7 Hz), 4.32(1H,m), 4.52(1H,dd,J=4.9, 6.8 Hz), 4.60(1H,dd,J=2.0, 4.9 Hz), 6.05(1H,d,J=6.8 Hz), 8.21(1H,s)

—Compound 6— yield: 55.2%
m.p.: 203°–203.5° C.
NMR($D_2O$): $\delta=2.50(3H,s)$, 3.55(3H,s), 3.84(1H,dd,J=2.9, 12.7 Hz), 3.96(1H,dd,J=2.4, 12.7 Hz), 4.13(1H,dd,J=2.9, 5.4 Hz), 4.42(1H,m), 4.91(1H,dd,J=5.4, 6.4 Hz), 6.00(1H,d,J=6.4), 8.23(1H,s)

[METHOD 2]

10 g of 5-amino-1-β-D-ribofuranosyl-4-imidazolecarbonitrile was dissolved in 20% ammonia methanol solution. 10 ml of acetonitrile was added thereto and the solution was heated for 5 hours at 180° C. The solvent was distilled off, purified by silica gel column chromatography and recrystallized from methanol to give 4.2 g of 2-methyladenosine (yield: 35.9%). 2-methyladenosine was methylated in the same manner as the above-mentioned [METHOD 1] to give Compound 5 and Compound 6.

Example 4

Using isobutylnitrile instead of acetonitrile, 2-isopropyl-2'-O-methyladenosine (Compound 7) and 2-isopropyl-3'-O-methyladenosine (Compound 8) were obtained in the same manner as Example 2 [METHOD 2].

—Compound 7—

NMR($D_2O$): $\delta=1.25(6H,d,J=7$ Hz), 2.99(1H,sep.,J=7 Hz), 3.39(3H,s), 3.83(1H,dd,J=3.3, 12.9 Hz), 3.91(1H,dd,J=2.6, 12.9 Hz), 4.29(1H,m), 4.58(1H,dd,J=4.9, 6.4 Hz), 4.63(1H,dd,J=2.4, 4.9 Hz), 6.07(1H,d,J=6.4 Hz)

—Compound 8—

NMR($D_2O$): $\delta=1.35(6H,d,J=6.9$ Hz), 3.14(1H,sep.,J=6.9 Hz), 3.54(3H,s), 3.84(1H,dd,J=4.1, 12.8 Hz), 3.94(1H,dd,J=3.0, 12.8 Hz), 4.24(1H,dd,J=5.4, 5.4 Hz), 4.36(1H,m), 5.03(1H,dd,J=5.4, 5.4 Hz), 6.08(1H,d J=5.4 Hz), 8.34(1H,s)

Example 5

6-chloro-2-methyl-9-β-D-ribofuranosyl-9H-purine was treated in the same manner as Example 2 to give 6-chloro-2-methyl-9-(3,5-O-TIPDS-β-D-ribofuranosyl)-9H-purine. After the 2'-position of the compound was O-ethylated by using ethyl iodide, 6-position of the compound was aminated by using ammonia. The protecting group, TIPDS, was removed to give 2-methyl-2'-O-ethyladenosine (Compound 9).

NMR($D_2O$): $\delta=1.07(3H,dd,J=6.8$, 6.8 Hz), 2.52(3H,s), 3.38(3H,s), 3.48–3.57(1H,m), 3.64–3.73(1H,m), 3.86(1H,dd,J=2.9, 12.7 Hz), 3.94(1H,dd,J=2.4, 12.7 Hz), 4.35(lh,ddd,J=2.0, 2.4, 2.9 Hz), 4.59(1H,dd,J=2.0, 4.9 Hz), 4.68(1H,dd,J=4.9, 7.3 Hz), 6.07(1H,d,J=7.3 Hz), 8.25(1H,s)

Using butyl iodide instead of ethyl iodide, 2'-O-butylation was carried out to give 2-methyl-2'-O-n-butyladenosine (Compound 10) in the same manner.

NMR($CDCl_3$): $\delta=0.79(3H,t,J=7.3$ Hz), 1.22(2H,qt,J=7.3, 7.3 Hz), 1.39(2H,ddt,J=7.3, 7.3, 7.3 Hz), 2.56(3H,s), 3.33(1H,m), 3.47(1H,m), 3.74(1H,ddd,J=1.5, 13.7, 14.2 Hz), 3.96(1H,ddd,J=1.5, 2.0, 13.7 Hz), 4.35(1H,m), 4.51(1H,d,J=4.4 Hz), 4.78(1H,dd,J=4.4, 7.8 Hz), 5.64(2H,brs,$D_2O$-exchangeable), 5.78(1H,d,J=7.8 Hz), 7.02(1H,dd,J=2.0, 14.2 Hz,$D_2O$-exchangeable), 7.74(1H,s)

Example 6

14 ml of 2,2-dimethoxypropane, 16 ml of acetone and 1.3 g of p-toluenesulfonic acid were added to 1.5 g of 6-chloro-9-β-D-ribofuransyl-9H-purine, and the reaction mixture was stirred for 2 hours at room temperature to give 6-chloro-9-(2,3-O-isopropylidene-β-D-ribofuranosyl)-9H-purine. The solution was concentrated to dryness and separated with chloroform/water. The chloroform layer was washed and dried over sodium sulfate anhydride. After the solvent was distilled off, the residue was dissolved in 30 ml of acetone. 30 ml of methyl iodide and 1.2 g of silver oxide were added to the solution and 5'-O-methyl-2',3'-O-isopropylideneadenosine was obtained in the same manner as Example 2 (iv). After filtration, the solution was concentrated to dryness, and the residue was dissolved in 20% ammonia methanol solution to be aminated. The solvent was distilled off and 90% formic acid was added thereto, and then the solution was stirred for 30 minutes at room temperature to remove the protecting group. The solution was concentrated to dryness under reduced pressure and recrystallized from ethanol to give 1.1 g of 5'-O-methyladenosine (Compound 11).

NMR($D_2O$): $\delta=3.43(3H,s)$, 3.71–3.82(2H,m), 4.33(1H,m), 4.43(1H,dd,J=5.4, 5.4 Hz), 4.78(1H,dd,J=5.4, 5.4 Hz), 6.12(1H,d,J=5.4 Hz), 8.31(1H,s), 8.41(1H,s)

Using butyl iodide instead of methyl iodide, 5'-O-butylation was carried out to give 5'-O-n-butyladenosine (Compound 12) in the same manner.

NMR($D_2O$): $\delta=0.94(3H,t,J=7.3$ Hz), 1.41(2H,qt,J=7.3, 7.3 Hz), 1.60(2H,tt,J=7.3, 7.3 Hz), 3.54(2H,m), 3.66(1H,dd,J=3.4, 11.2 Hz), 3.78(1H,dd,J=2.9, 11.2 Hz), 4.19(1H,m), 4.34(1H,dd,J=4.9, 4.9 Hz), 4.55(1H,dd,J=4.4, 4.9 Hz), 6.05(1H,d,J=4.4 Hz), 8.19(1H,s), 8.40(1H,s)

Example 7

In the same manner as Example 1 [METHOD 1], 5'-O-methyladenosine was methylated by using diazomethane and separated by ion exchange column chromatography to give 2',5'-O-dimethyladenosine (Compound 13) and 3',5'-O-dimethyladenosine (Compound 14).

—Compound 13—

NMR($D_2O$): $\delta=3.41(3H,s)$, 3.46(3H,s), 3.67–3.76(2H,m), 4.27(1H,m), 4.40(1H,dd,J=4.4, 4.9 Hz), 4.52(1H,dd,J=4.9, 5.4 Hz), 6.07(1H,d,J=5.4 Hz), 6.07(1H,d,J=5.4 Hz), 8.10(1H,s), 8.26(1H,s)

—Compound 14—

NMR (D$_2$O): δ=3.42(3H,s), 3.47(3H,s), 3.68–3.77(2H,m) 4.30(1H,m), 4.50(1H,dd,J=4.9, 5.4 Hz), 4.57(1H,dd,J=4.4, 4.9 Hz), 6.2(1H,d,J=5.4 Hz), 8.23(1H,s), 8.35(1H,s)

Example 8

In the same manner as Example 6, 6-chloro-9-β-D-ribofuranosyl-9H-purine was isopropylidenated, and methylated at the 5'-O-position by using methyl iodide. After 6-position of the compound was aminated by ammonia, the protecting group was removed to give 2,5'-O-dimethyladenosine (Compound 15).

NMR(D$_2$O): δ=2.55(3H,s), 3.41(3H,s), 3.73–3.78(2H,m), 4.32(1H,m), 4.42(1H,dd,J=4.9, 4.9 Hz), 4.77(1H,dd,J=4.9, 4.9 Hz), 6.07(1H,d,J=4.9 Hz), 8.25(1H,s)

Using butyl iodide instead of methyl iodide, 5'-O-butylation was carried out to give 2-methyl-5'-O-n-butyladenosine (Compound 16) in the same manner.

NMR(CD$_3$OD): δ=0.95(3H,t,J=7.3 Hz), 1.40(2H,qt,J=7.3, 7.3 Hz), 1.60(2H,tt,J=7.3, 7.3 Hz), 2.51(3H,s), 3.50–3.70(3H,m), 3.781H,dd,J=2.9, 10.7 Hz), 4.171H,m), 4.34(1H,dd,J=4.9, 4.9 Hz), 4.52(1H,dd,J=4.4, 4.9 Hz), 6.00(1H,d,J=4.4 Hz), 8.11(1H,s)

Example 9

6-chloro-9-β-D-ribofuranosyl-9H-purine was treated in the same manner as Example 2 to give 6-chloro-9-(3,5-O-TIPDS-β-D-ribofuranosyl)-9H-purine. After the compound was 2'-O-methylated, the 6-position of the compound was methylaminated by methylamine to give N$^6$-2'-O-dimethyladenosine (Compound 17).

NMR(D$_2$O): δ=3.00(3H,s), 3.40(3H,s), 3.81(1H,dd,J=3.4, 12.7 Hz), 3.89(1H,dd,J=2.9, 12.7 Hz), 4.26(1H,ddd,J=2.9, 3.4, 3.4 Hz), 4.44(1H,dd,J=5.4, 6.4 Hz), 4.57(1H,dd,J=3.4, 5.4 Hz), 6.03(1H,d,J=6.4 Hz), 8.10(1H,s), 8.19(1H,s)

Using butylamine instead of methylamine, N$^6$-n-butyl-2'-O-methyladenosine (Compound 18) was obtained in the same manner.

NMR(CDCl$_3$): δ=0.95(3H,t,J=7.3 Hz), 1.43(2H,qt,J=7.3, 7.3 Hz), 1.65(2H,tt,J=7.3, 7.3 Hz), 3.32(3H,s), 3.61(3H,m), 3.73(1H,m), 3.94(1H,m), 4.33(1H,m), 4.57(1H,d,J=4.4 Hz), 4.73(1H,dd,J=4.4, 7.8 Hz), 5.81(1H,d,J=7.8 Hz), 5.93(1H,brs,D$_2$O-exchangeable), 6.96(1H,brs,D$_2$O-exchangeable), 7.74(1H,s), 8.32(1H,s)

Example 10

In the same manner as Example 6, 6-chloro-9-β-D-ribofuranosyl-9H-purine was isopropylidenated. After 5'-O-methylation, the 6-position of the compound was methylaminated by methylamine to give N$^6$-5'-O-dimethyladenosine (Compound 19).

NMR(D$_2$O): δ=3.05(3H,s), 3.40(3H,s), 3.68–3.79(2H,m), 4.29(1H,m), 4.38(1H,dd,J=4.9, 5.4 Hz), 4.72(1H,dd,J=4.9, 5.4 Hz), 6.03(1H,d,J=4.9 Hz), 8.17(1H,s), 8.23(1H,s)

Using butylamine instead of methylamine, N$^6$-n-butyl-5'-O-methyladenosine (Compound 20) was obtained in the same manner.

NMR(CDCl$_3$): δ=0.95(3H,t,J=7.3 Hz), 1.44(2H,qt,J=7.3, 7.3 Hz), 1.66(2H,tt,J=7.3, 7.3 Hz), 3.33(3H,s), 3.54–3.68(4H,m), 4.35–4.45(3H,m), 5.87(1H,brs,D$_2$O exchangeable), 5.93(1H,d,J=5.9 Hz), 8.00(1H,s), 8.28(1H,s)

Example 11

6-chloro-2-methyl-9-β-D-ribofuranosyl-9H-purine was treated in the same manner as mentioned above to give 6-chloro-2-methyl-9-(3,5-O-TIPDS-β-D-ribofuranosyl)-9H-purine or 6-chloro-2-methyl-9-(2,3-O-isopropylidene-β-D-ribofuranosyl)-9H-purine, and then the resulting compound was 2'-O-alkylated or 5'-O-alkylated. After the 6-position of the compound was aminated or alkylaminated by ammonia or alkylamine, the protecting group, TIPDS or isopropylidene, was removed to give the following compounds.

2,N$^6$,2'-O-trimethyladenosine (Compound 21)

NMR(D$_2$O): δ=2.40(3H,s), 2.97(3H,s), 3.37(3H,s), 3.81(1H,dd,J=2.9, 12.7 Hz), 3.90(1H,dd,J=2.9, 12.7 Hz), 4.29(1H,m), 4.44(1H,dd,J=4.9, 6.8 Hz), 4.57(1H,dd,J=2.4, 4.9 Hz), 5.96(1H,d,J=6.8 Hz), 8.06(1H,s)

2,N$^6$-dimethyl-2'-O-ethyladenosine (Compound 22)

NMR(D$_2$O): δ1.05(3H,dd,J=6.8, 6.8 Hz), 2.50(3H,s), 3.09(3H,s), 3.37(3H,s), 3.46–3.74(2H,m), 3.85(1H,dd,J=2.9, 13.2 Hz), 3.93(1H,dd,J=2.4, 13.2 Hz), 4.34(1H,m), 4.56(1H,dd,J=1.5, 4.9 Hz), 4.63(1H,dd,J=5.4, 6.8 Hz), 6.02(1H,d,J=6.8 Hz), 8.15(1H,s)

N$^6$-n-butyl-2,2'-O-dimethyladenosine (Compound 23)

NMR(CDCl$_3$): δ=0.94(3H,t,J=7.3 Hz), 1.43(2H,qt,J=7.3, 7.3 Hz), 1.63(2H,tt,J=7.3, 7.3 Hz), 2.54(3H,s), 3.32(3H,s), 3.62(2H,m), 3.74(1H,m), 3.95(1H,dd,J=1.5, 2.7 Hz), 4.33(1H,m), 4.56(1H,d,J=4.4 Hz), 4.74(1H,dd,J=4.4, 7.8 Hz), 5.77(1H,d,J=7.8 Hz), 5.79(1H,brs,D$_2$O-exchangeable), 7.33(1H,brs,D$_2$O-exchangeable), 7.66(1H,s)

2,N$^6$,5'-O-trimethyladenosine (Compound 24)

NMR(D$_2$O): δ=2.52(3H,s), 3.10(3H,s), 3.41(3H,s), 3.68–3.78(2H,m), 4.30(1H,m), 4.40(1H,dd,J=4.9, 4.9 Hz), 4.72(1H,dd,4.9, 4.9 Hz), 6.05(1H,d,J=4.9 Hz), 8.20(1H,s)

N$^6$-n-butyl-2,5'-O-dimethyladenosine (Compound 25)

NMR(CDCl$_3$): δ=0.95(3H,t,J=7.3 Hz), 1.43(2H,qt,J=7.3, 7.3 Hz), 1.64(2H,tt,J=7.3, 7.3 Hz), 2.52(3H,s), 3.5–3.7(4H,m), 4.3–4.4(3H,m), 5.77(1H,brs,D$_2$O-exchangeable), 5.87(1H,d,J=5.9 Hz), 7.91(1H,s)

Example 12

1 g of 2,2'-O-dimethyladenosine (Compound 5) was dissolved in 5 ml of dimethylformamide, and 2 ml of methyl iodide was added thereto and the solution was stirred for 30 to 40 minutes. After the solvent was distilled off, 5 ml of 0.5N sodium hydroxide was added and the solution was heated for 75 minutes at 100° C. The solution was neutralized and desalted by hydrophobic column chromatography, and then recrystallized from methanol to give 2,N$^6$,2'-O-trimethyladenosine (Compound 21).

In the same manner, 2,3'-O-dimethyladenosine was used as a starting material to give 2,N$^6$,3'-O-trimethyladenosine (Compound 26).

NMR(D$_2$O): δ=2.46(3H,s), 3.05(3H,s), 3.56(3H,s), 3.84(1H,dd,J=3.4, 12.7 Hz), 3.96(1H,dd,J=2.0, 12.7 Hz), 4.11(1H,m), 4.41(1H,m), 4.86(1H,t-like, J=5.9 Hz), 5.94(1H,d,J=5.9 Hz), 8.10(1H,s)

Example 13

(i) 500 ml of acetic anhydride and 500 ml of pyridine were added to 45 g of guanosine, and the reaction mixture was stirred for 12 hours at room temperature. The precipitated crystalline was separated by filtration and washed with water. The filtrate was concentrated under reduced pressure, and the precipitated crystalline was obtained by filtration. The first and second crystals were put together to give 2',3',5'-O-triacetylguanosine (yield: 94.4%). (ii) 375 ml of phosphoruos oxychloride and 20 ml of diethylaniline was added to 55 g of 2',3',5'-O-triacetylguanosine, and the reaction mixture was refluxed with heating for 3 minutes. The solution was concentrated to 100 ml under reduced pressure, poured into ice-cold water and extracted with dichloromethane. The dichloromethane layer was washed to be neutralized and dried over sodium sulfate anhydrate. After purification by silica gel column chromatography, the solution was concentrated under reduced pressure to give 40 g of 6-chloro-2-amino-9-(2,3,5-O-triacetyl-$\beta$-D-ribofuranosyl)-9H-purine (yield 69%).

(iii) 4.5 g of the resulting product was dissolved in 40 ml of cooled hydrochloric acid. 1.05 g of sodium nitrite dissolved in 3 ml of water was slowly added to the solution with stirring. The reaction mixture was neutralized by cooled ammonia water and extracted with dichloroethane. The dichloroethane layer was dried over sodium sulfate anhydride and concentrated to dryness to give 2,6-dichloro-9-(2,3,5-O-triacetyl-$\beta$-D-ribofuranosyl)-9H-purine.

(iv) The above residue was 100 ml of 20% ammonia methanol solution and heated for 8 hours at 70° C. in an autoclave to give 2-chloroadenosine.

(v) In the same manner as Example 1 [METHOD 1], 2-chloroadenosine was methylated to give 2-chloro-2'-O-methyladenosine (Compound 27) and 2-chloro-3'-O-methyladenosine (Compound 28).

—Compound 27—

NMR(D$_2$O): $\delta$=3.43(3H,s), 3.84(1H,dd,J=3.4, 13.2 Hz), 3.92(1H,dd,J=2.5, 13.2 Hz), 4.30(1H,m), 4.40(1H,dd,J=6.8, 4.9 Hz), 4.60(1H,dd,J=3.4, 4.9Hz), 6.05(1H,d,J=6.8 Hz), 8.28(1H,s)

—Compound 28—

NMR(D$_2$O): $\delta$=3.53(3H,s), 3.83(1H,dd,J=3.4, 12.9 Hz), 3.95(1H,dd,J=2.6, 12.9 Hz), 4.12(1H,dd,J=5.9, 5.9 Hz), 4.38(1H,m), 4.87(1H,dd,J=5.9, 5.9 Hz), 5.98(1H,d,J=5.9 Hz), 8.27(1H,s)

Example 14

3 g of 2-amino-2'-O-methyladenosine, the Compound 30 in Example 15, was dissolved in 35 ml of 42% fluoboric acid. 1.3 g/10 ml aqueous solution of sodium nitrite was added to the solution with stirring at −5° C. to −10° C. and stirred for one hour. The reaction mixture was cooled to −20° C. and neutralized by 50% sodium hydroxide aqueous solution. The solution was desalted by hydrophobic column chromatography and crystallized from methanol to give 697 mg of 2-fluoro-2'-O-methyladenosine (Compound 29).

Yield: 23%

NMR(D$_2$O): $\delta$=3.45(3H,s), 3.84(1H,dd,J=3.9, 13.2 Hz), 3.91(1H,dd,J=2.9, 13.2 Hz), 4.27(1H,m), 4.50(1H,dd,J=5.9, 6.4 Hz), 4.60(1H,dd,J=3.4, 5.9 Hz), 6.06(1H,d,J=6.4 Hz), 8.29(1H,s)

Example 15

The 6-position of 2-amino-6-chloro-9-(2,3,5-O-triacetyl-$\beta$-D-ribofuranosyl)-9H-purine was aminated by ammonia to give 2-aminoadenosine. In the same manner as Example 1 [METHOD 1], 2-aminoadenosine was methylated to give 2-amino-2'-O-methyladenosine (Compound 30) and 2-amino-3'-O-methyladenosine (Compound 31).

—Compound 30— m.p.: 104°–108° C. (decomposition)

NMR(D$_2$O): $\delta$=3.41(3H,s), 3.81(1H,dd,J=3.4, 12.7 Hz), 3.88(1H,dd,J=2.9, 12.7 Hz), 4.26(1H,m), 4.49(1H,dd,J=4.9, 6.8 Hz), 4.57(1H,dd,J=2.9, 4.9 Hz), 5.95(1H,dd,J=6.8 Hz), 8.00(1H,s)

—Compound 31— m.p.: 228–228.5° C.

NMR(D$_2$O): $\delta$=3.52(3H,s), 3.80(1H,dd,J=3.4, 12.7 Hz), 3.91(1H,dd,J=2.9, 12.7 Hz), 4.09(1H,dd,J=2.9, 5.4 Hz), 4.35(1H,m), 4.87(1H,dd,J=5.4, 6.4 Hz), 5.89(1H,d,J=6.4 Hz), 7.99(1H,s)

The following descriptions serve to illustrative pharmaceutical studies of the compounds of the present invention.

(1) Acute toxicity test

The test compounds of the present invention, which were dissolved or suspended in 0.5% carboxymethylcellulose (C.M.C.) aqueous solution, were orally administered to groups of 4 to 16 ddY-strain male mice, and the LD$_{50}$ values were calculated based on the death rate for 7 days thereafter. An example of the results is shown in Table 1.

TABLE 1

| Test Compound | LD$_{50}$ (mg/kg) |
| --- | --- |
| Compound 1 | >2,000 |
| Compound 2 | >2,000 |
| Compound 3 | 750–1,000 |
| Compound 5 | 540 |
| Compound 9 | 500–1,000 |
| Compound 11 | 800 |
| Compound 15 | 500–1,000 |
| Compound 17 | 1,000–2,000 |
| Compound 19 | 1,300 |
| Compound 21 | about 400 |
| Compound 22 | about 400 |
| Compound 24 | 1,320 |
| Compound 27 | about 400 |
| Compound 29 | >2,000 |

(2) Antihypertensive activity

The test compounds, which were dissolved or suspended in 0.5% C.M.C. aqueous solution, were orally administered to groups of 3 or 4 spontaneously hypertensive rats (SHR), weighing about 300 to 400 g. Blood pressure was measured before and 2, 4 and 6 hours after the administration. An example of the results is shown in Table 2. Data show the mean value ± S.E.

TABLE 2

| | Blood pressure (mmHg) | | | |
| --- | --- | --- | --- | --- |
| Test Compound (Dose mg/kg) | Before | 2 hrs [Decrease] | 4 hrs [Decrease] | 6 hrs [Decrease] |
| Control | 219 ± 10 | 217 ± 12 | 225 ± 17 | 222 ± 12 |

TABLE 2-continued

| Test Compound (Dose mg/kg) | Before | Blood pressure (mmHg) 2 hrs [Decrease] | 4 hrs [Decrease] | 6 hrs [Decrease] |
|---|---|---|---|---|
| | | [1.5%] | [−2.6%] | [−1.4%] |
| Compound 1 (200) | 218 ± 21 | 103 ± 21 [53.2%] | 121 ± 32 [45.8%] | 128 ± 41 [42.8%] |
| Compound 2 (200) | 227 ± 12 | 135 ± 28 [41.2%] | 163 ± 40 [29.0%] | 167 ± 47 [27.2%] |
| Compound 3 (100) | 215 ± 14 | 102 ± 15 [52.2%] | 106 ± 20 [49.5%] | 111 ± 26 [47.3%] |
| Compound 5 (10) | 220 ± 11 | 131 ± 6 [40.2%] | 161 ± 11 [26.5%] | 193 ± 24 [12.7%] |
| Compound 9 (30) | 221 ± 2 | 169 ± 7 [23.6%] | 197 ± 5 [10.7%] | 191 ± 9 [13.5%] |
| Compound 11 (30) | 218 ± 5 | 189 ± 3 [18.2%] | 206 ± 10 [5.9%] | 204 ± 9 [6.6%] |
| Compound 15 (10) | 237 ± 8 | 154 ± 13 [35.2%] | 195 ± 22 [17.7%] | 215 ± 5 [9.1%] |
| Compound 17 (30) | 231 ± 3 | 192 ± 15 [17.1%] | 204 ± 5 [11.7%] | 199 ± 8 [14.1%] |
| Compound 19 (30) | 213 ± 10 | 122 ± 8 [43.0%] | 155 ± 7 [27.1%] | 157 ± 12 [26.3%] |
| Compound 21 (30) | 207 ± 6 | 159 ± 20 [23.9%] | 172 ± 7 [16.9%] | 188 ± 8 [10.8%] |
| Compound 22 (10) | 227 ± 7 | 168 ± 6 [25.8%] | 185 ± 7 [18.8%] | 197 ± 3 [13.1%] |
| Compound 24 (10) | 226 ± 4 | 128 ± 7 [43.3%] | 165 ± 7 [27.0%] | 174 ± 4 [23.0%] |
| Compound 27 (100) | 221 ± 9 | 70 ± 10 [68.4%] | 78 ± 8 [64.8%] | 73 ± 16 [66.9%] |
| Compound 29 (30) | 245 ± 12 | 131 ± 4 [45.9%] | 195 ± 5 [19.8%] | 204 ± 3 [16.4%] |
| Adenosine (200) | 191 ± 9 | 202 ± 12 [−6.1%] | 187 ± 3 [1.8%] | 198 ± 4 [−3.2%] |

As shown by the above-mentioned results, the compounds of the present invention have excellent hypotensive effects even at low doses. However, adenosine does not decrease blood pressure at oral administration.

Bradycardia was observed at the administration of adenosine or 2-substituted adenosines, however, the compounds of the present invention O-alkylated at the 2-or 3-position of ribose did not show such a side effect.

Thus the compounds of the present invention have excellent antihypertensive effect at oral administration and do not have side effect such as bradycardia. Therefore, the compounds of the present invention are not only useful as antihypertensive drugs for oral administration, but also as drugs for various diseases caused by hypertension, e.g., cerebrovascular disease such as cerebral hemorrhage, cerebral infarction or subarachnoidal hemorrhage, cardiopathy such as congestive heart failure, myocardial infarction or sudden cardiac death, and renal insufficiency.

The compounds of the present invention can be made into pharmaceutical compositions by combination with appropriate medicinal carriers or diluents, and can be formulated into preparations in solid, semisolid, liquid or gaseous form such as tablets, capsules, powders, granules, ointments, solutions, suppositories, injections, inhalants, aerosols and cataplasms in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention can also be made into an ointment by combination with an ointment base such as vaseline, paraffin, plastibase, simple ointment, hydrophilic ointment, hydrophilic vaseline or hydrophilic plastibase.

Furthermore, the compounds of the invention can be made into a suppository by mixing with a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or nonaqueous solvent, such as distilled water for injection, physiologically saline solution, vegetable oil, synthetic aliphatic acid glycerides, esters of higher aliphatic acid or propylene glycol.

In case of inhalations or aerosol preparations, the compounds of the invention in the form of a liquid or minute powder can be filled up in an aerosol container with gas or liquid spraying agent, and if desired, with conventional adjuvants such as humidifying agents or dispersing agent. They can also be used as pharmaceuticals for a non-pressurized preparation such as in a nebulizer or an atomizer.

Cataplasms can be prepared by mixing the compounds with mentha oil, concentrated glycerin, kaolin or other suitable additives.

The desirable dose of the compounds of the present invention varies with the subject, form of the drug, method and period of administration. However, in order to obtain desirable effects, generally it is recommended to administer orally 0.2 to 5,000 mg, preferably 1 to 3,000 mg daily. Unit preparations are also recommended for administration in one to several units daily.

In case of parenteral administrations e.g. injections, doses of the compounds in the order of one tenth to one second of the above dose are preferable as daily doses.

Some prescriptions of the pharmaceutical compositions are shown below as examples which contain the compounds of the present invention as active ingredients.

| Prescription example 1 (tablet) | |
|---|---|
| Component | Content in a tablet (mg) |
| compound of this invention | 25 |
| lactose | 175 |
| corn starch | 40 |
| magnesium stearate | 10 |
| Total | 250 mg |

| Prescription example 2 (capsule) | |
|---|---|
| Component | Content in a capsule (mg) |
| compound of this invention | 50 |
| lactose | 250 |
| Total | 300 mg |

| Prescription example 3 (inhalation) | |
|---|---|
| Component | Content in a inhalation (g) |
| compound of this invention | 1 |
| lactose | 5 |
| Total | 6 g |

Prescription example 4 (injection)

| -continued | |
|---|---|
| Component | Content in an ampule (mg) |
| compound of this invention | 10 |
| sodium chloride | proper amount |
| distilled water for injection | proper amount |
| Total | 1 ml |

| Prescription example 5 (ointment) | |
|---|---|
| Component | Weight (g) |
| compound of this invention | 1 |
| emulsified wax | 30 |
| white petrolatum | 50 |
| liquid paraffin | 20 |
| Total | 101 g |

What is claimed is:

1. An adenosine compound having the formula (I):

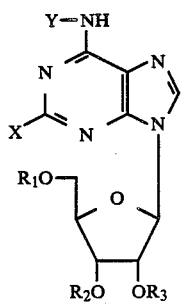

wherein each of $R_1$, $R_2$ and $R_3$, which may be the same or different, is hydrogen or a lower alkyl group, and at least one of $R_1$, $R_2$, and $R_3$ is a lower alkyl group; X is hydrogen, a lower alkyl group, an amino group or halogen; and Y is hydrogen or a lower alkyl group; or pharmaceutically acceptable salt thereof.

2. An adenosine compound or pharmaceutically acceptable salt thereof according to claim 1 wherein $R_1$ is a lower alkyl group.

3. An adenosine compound or pharmaceutically acceptable salt thereof according to claim 2 wherein X is a lower alkyl group.

4. An adenosine compound or pharmaceutically acceptable salt thereof according to claim 2 wherein Y is a lower alkyl group.

5. An adenosine compound or pharmaceutically acceptable salt thereof according to claim 1 wherien $R_3$ is a lower alkyl group.

6. An adenosine compound or pharmaceutically acceptable salt thereof according to claim 5 wherein X is a lower alkyl group.

7. An adenosine compound or pharmaceutically acceptable salt thereof according to claim 5 wherein Y is a lower alkyl group.

8. An adenosine compound or pharmaceutically acceptable salt thereof according to claim 1 wherein X is halogen.

9. An antihypertensive composition comprising as an active ingredient an effective amount of at least one adenosine compound of the formula (I):

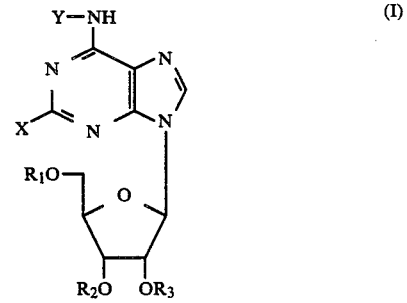

wherein each of $R_1$, $R_2$ and $R_3$, which may be the same or different, is hydrogen or a lower alkyl group, and at least one of $R_1$, $R_2$ and $R_3$ is a lower alkyl group; X is hydrogen, a lower alkyl group, an amino group or halogen; and Y is hydrogen or a lower alkyl group; or pharmaceutically acceptable salt thereof; and a pharmaceutically acceptable carrier.

10. An antihypertensive composition according to claim 9, which is formulated into a form suitable for oral administration.

11. A method for treating hypertension which comprises administering to an animal in need thereof an antihypertensive effective amount of at least one adenosine compound or pharmaceutically acceptable salt thereof of the formula (I):

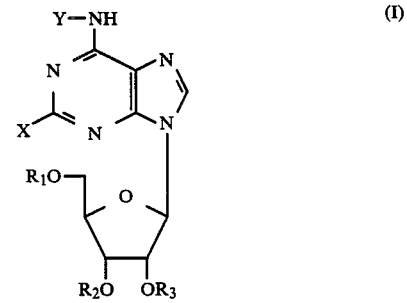

wherein each of $R_1$, $R_2$ and $R_3$, which may be the same or different, is hydrogen or a lower alkyl group, and at least one of $R_1$, $R_2$ and $R_3$ is a lower alkyl group; X is hydrogen, a lower alkyl group, an amino group or halogen; and Y is hydrogen or a lower alkyl group.

* * * * *